(12) United States Patent
Martino

(10) Patent No.: US 10,687,971 B2
(45) Date of Patent: Jun. 23, 2020

(54) PROTECTIVE SLEEVE AND TREATMENT METHOD THEREOF

(71) Applicant: Stephen John Martino, Farmingdale, NJ (US)

(72) Inventor: Stephen John Martino, Farmingdale, NJ (US)

(73) Assignee: THE LONNIE BRACE LLC, Farmingdale, NJ (US)

(*) Notice: Subject to any disclaimer, the term of this patent is extended or adjusted under 35 U.S.C. 154(b) by 372 days.

(21) Appl. No.: 15/680,121

(22) Filed: Aug. 17, 2017

(65) Prior Publication Data

US 2018/0028341 A1    Feb. 1, 2018

Related U.S. Application Data

(63) Continuation of application No. 15/657,191, filed on Jul. 23, 2017, and a continuation-in-part of application No. 15/657,191, filed on Jul. 23, 2017.

(60) Provisional application No. 62/367,508, filed on Jul. 27, 2016.

(51) Int. Cl.
*A61F 5/01* (2006.01)

(52) U.S. Cl.
CPC ............ *A61F 5/013* (2013.01); *A61F 5/0125* (2013.01); *A61F 2005/0165* (2013.01); *A61F 2005/0172* (2013.01); *A61F 2005/0174* (2013.01); *A61F 2005/0176* (2013.01)

(58) Field of Classification Search
CPC ...... A61F 5/013; A61F 5/0118; A61F 5/0104; A61F 5/0106; A61F 5/0109; A61F 2013/00093; A61F 13/061; A61F 2005/0172; A61F 2005/0176; A61F 2005/0174; A61F 2005/0165
See application file for complete search history.

(56) References Cited

U.S. PATENT DOCUMENTS

| 4,441,493 A | 4/1984 | Nirschl |
| 4,492,227 A * | 1/1985 | Senn .................. A61F 13/061 602/26 |
| 4,922,929 A | 5/1990 | DeJourneit |
| 5,063,913 A | 11/1991 | Nyi |
| 5,472,424 A | 12/1995 | Detty |
| 5,865,776 A | 2/1999 | Springs |
| 6,110,135 A | 8/2000 | Madow et al. |
| 6,224,564 B1 | 5/2001 | Korobow |
| 6,374,408 B1 | 4/2002 | Tomlinson et al. |
| 2002/0147419 A1 * | 10/2002 | Schuman ............. A61F 5/0118 602/5 |
| 2004/0153017 A1 | 8/2004 | Simmons |
| 2004/0193086 A1 | 9/2004 | Cofre |

(Continued)

*Primary Examiner* — Kari K Rodriquez
(74) *Attorney, Agent, or Firm* — Changi Wu; Changi Wu Law Office

(57) ABSTRACT

A protective sleeve for treating injury to a wearer's elbow joint comprises a central pad; a protective opening one wearer's medial elbow region, a cap attached on the exterior side of the central pad; a relatively thin sheet; a cylindrical sleeve formed by the relatively thin sheet and the central pad; a first compression strip attached on the interior side within the upper portion of the central pad; a second compression strip attached on the interior side within the lower portion of the central pad; and a fastening means for securing the protective sleeve on the wearer's arm; and a treatment method thereof.

16 Claims, 6 Drawing Sheets

(56) References Cited

U.S. PATENT DOCUMENTS

2011/0306911 A1    12/2011   Tran  
2014/0031733 A1*   1/2014   Martino ................ A61F 5/0118  
                                                                        602/16

* cited by examiner

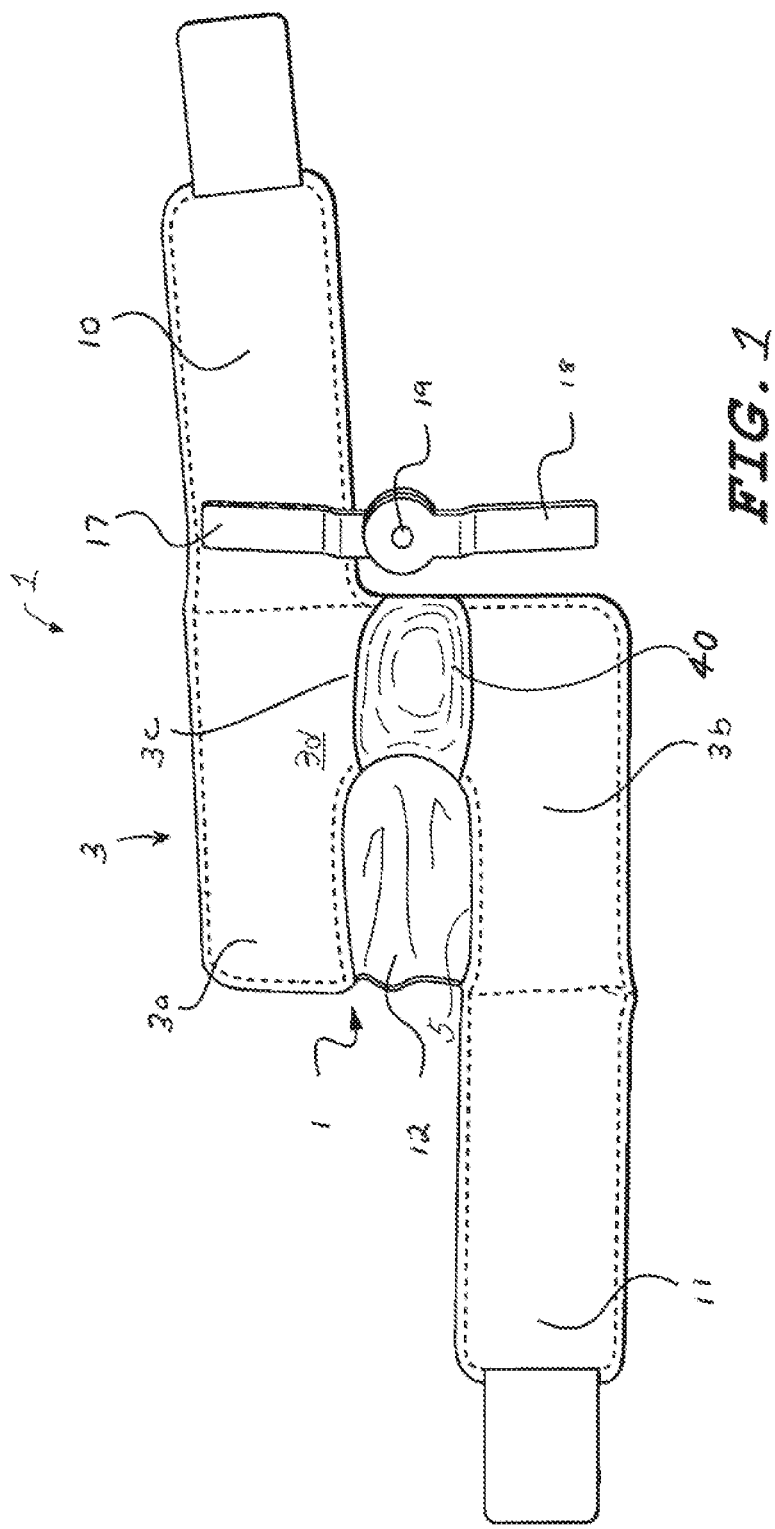

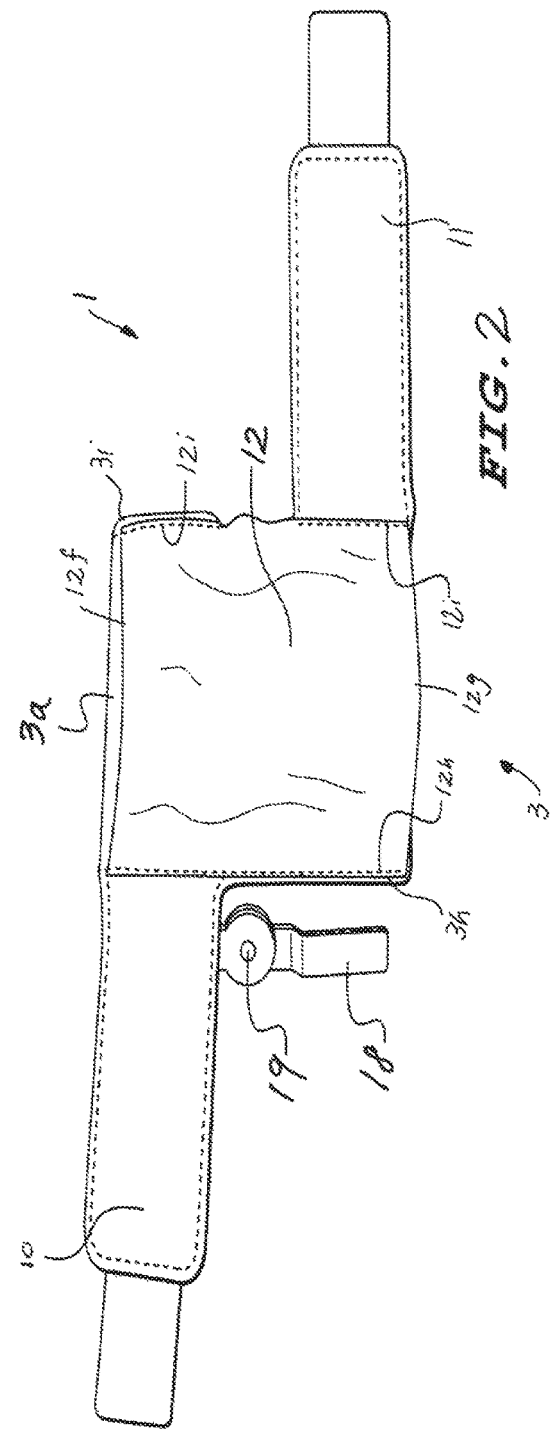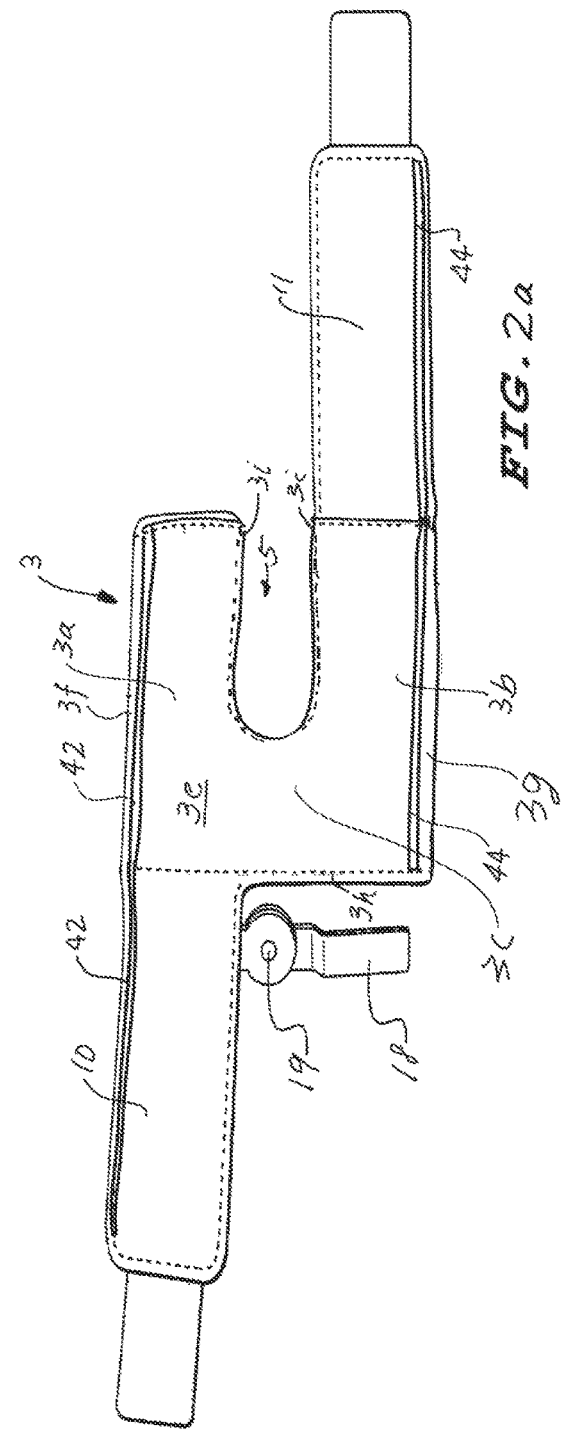

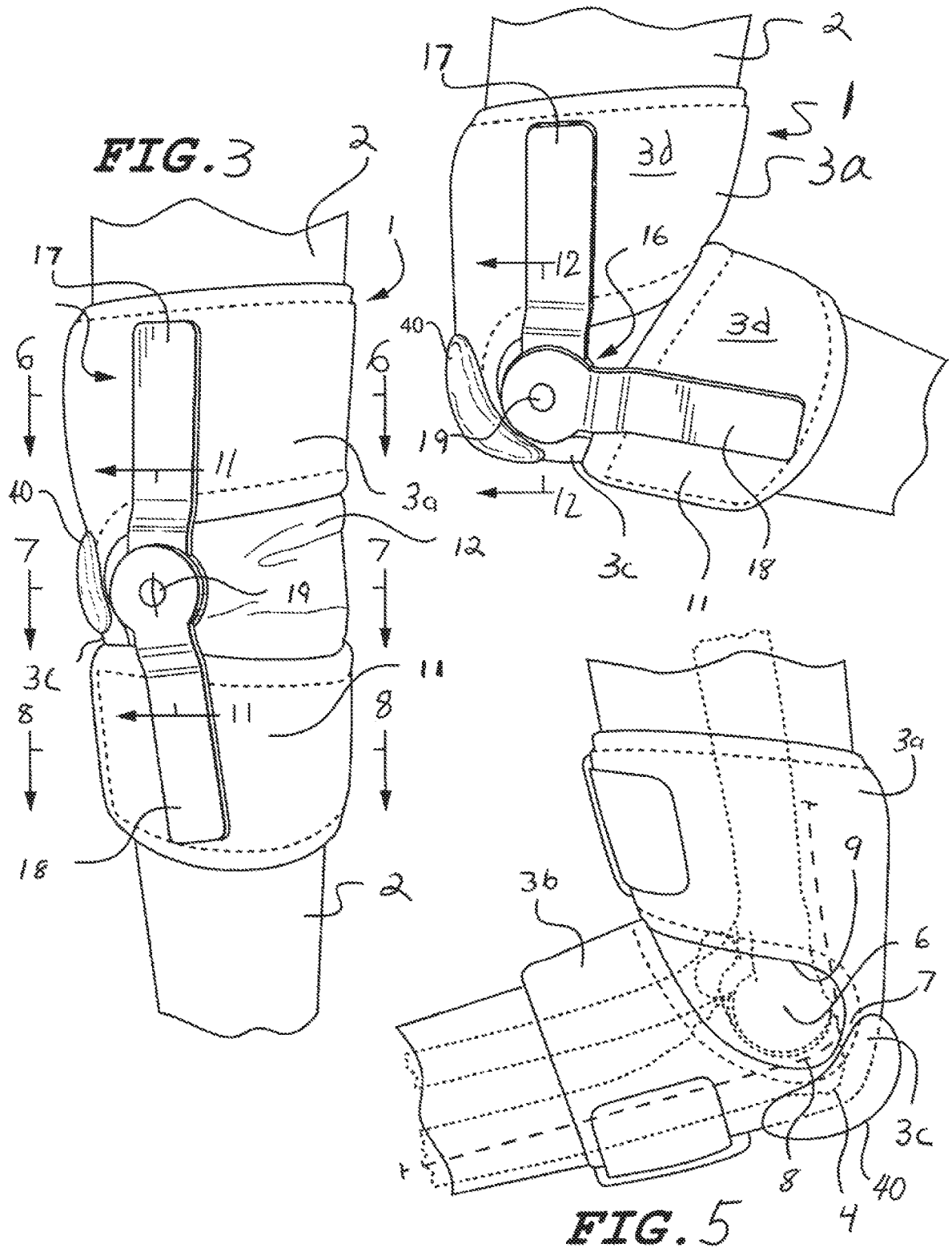

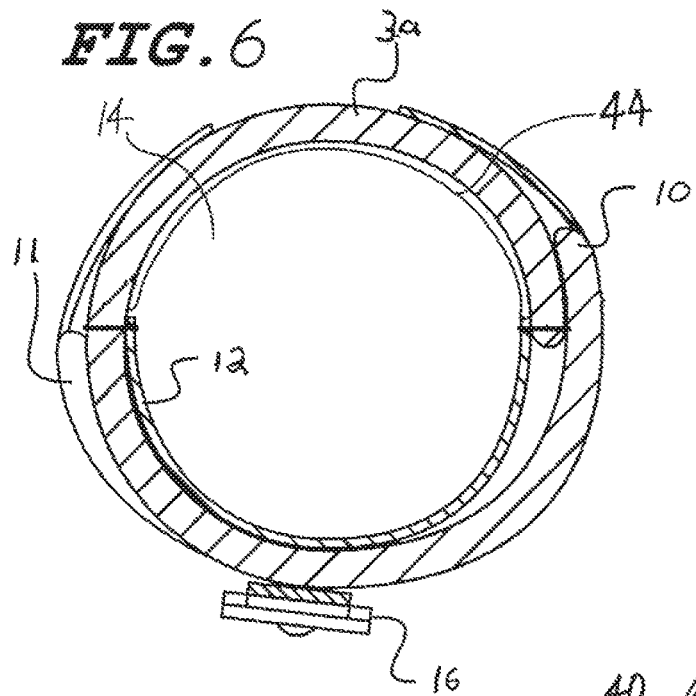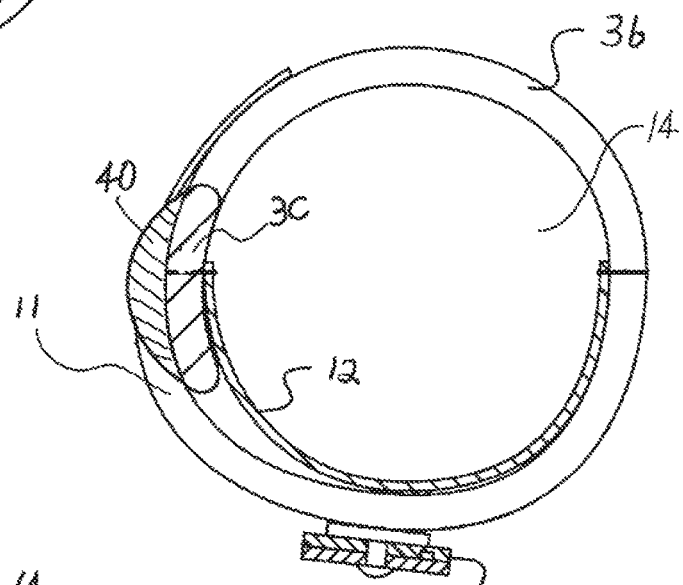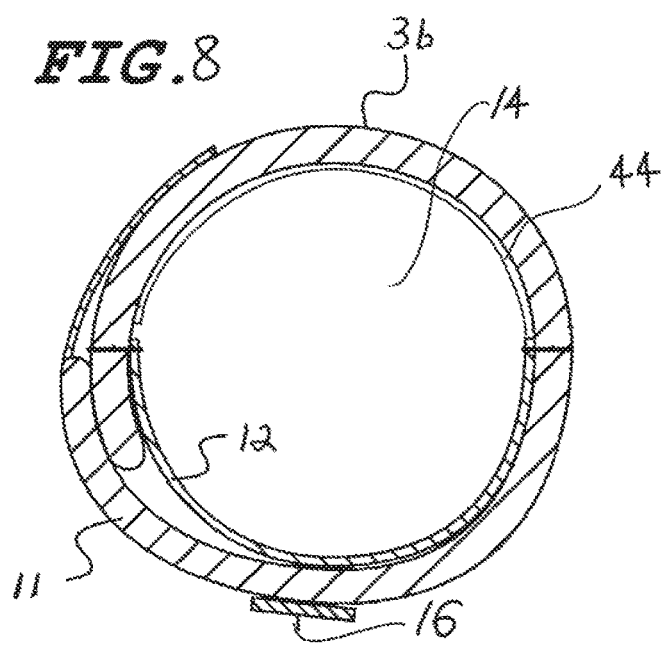

PROTECTIVE SLEEVE AND TREATMENT METHOD THEREOF

CROSS-REFERENCE RELATED TO RELATED APPLICATIONS

This application is a continuation-in-part of commonly-owned, same inventor, presently co-pending U.S. Nonprovisional patent application Ser. No. 15/657,191, filed Jul. 23, 2017, which is incorporated herein by reference in its entirety. The presently co-pending application Ser. No. 15/657,191 also claims the priority and benefit of U.S. Provisional Patent Application No. 62/367,508, filed Jul. 27, 2016.

BACKGROUND

Various externally applied elastic and rigid braces are in use that provide stability to the elbow and promote healing. One such common injury to the elbow is called "tennis elbow." This term commonly applies to painful inflammation of the tendons attached to the medial or lateral epicondyle of the humerus. As a result of such things as direct trauma, repetitive use, poor elbow positioning, surgery or mechanical strain, the elbow area can become painful and limit activity.

The ulnar nerve lies in an anatomical location commonly referred to as the cubital tunnel, which is located between the medial epicondyle of the humerus and the olecranon process of the ulna bone. Through soft tissue injury of the surrounding area, trauma, repetitive use of the arm, constant bending of the elbow, positioning of the arm, surgery and inflammation of the tendons attached to the medial epicondyle of the humerus, the ulnar nerve can be injured. This injury could cause reversible and irreversible changes to the ulnar nerve. An ulnar nerve injury in the cubital tunnel can result in a person suffering both numbness and weakness of the hand along with weakness of some forearm muscles.

Treatments for tendonitis pertaining to the medial or lateral epicondyle of the humerus such as tennis elbow, irritation and/or inflammation of the cubital tunnel and/or surrounding tissues, and ulnar nerve injury, have usually been rather conservative. Such treatments have comprised rest, positioning and anti-inflammatory medication. Occasionally hydrocortisone injection, ulnar nerve transpositions, and tendon surgery have been utilized, with varying degrees of success.

Certain braces have been used to support and stabilize the elbow. These braces were designed to directly cushion the medial epicondyle of the humerus and surrounding structures.

For several reasons, current braces fail to adequately treat injuries to the cubital tunnel and surrounding soft tissues, ulnar nerve compression/injury in the cubital tunnel, tennis elbow (pertaining to tendonitis of the medial epicondyle of the humerus) or other similar muscular and nerve disorders in the region of the elbow. First, several current braces place contact on the medial elbow region, which applies direct and constant pressure to the injured medial aspect area of the elbow. Second, several of the foregoing braces aggravate the structures of the injured area such as medial elbow region of the elbow through friction due to tightening of the brace during movement. Third, several of the foregoing braces fail to isolate the injured area of the medial elbow. Fourth, several of these foregoing braces do not adequately permit healing in the area because of the constant pressure applied at the injured medial area of the elbow. Fifth, the current braces do not provide counter-force to the forearm to reduce tension, strain, and inflammation on the tendon insertions to the medial and lateral epicondyles. Sixth, several of these foregoing braces fail to distribute pressure away from the medial elbow area, thereby promoting healing. Seventh, several of these foregoing braces do not adequately restrain movement of the elbow joint with a lateral support structure. Finally, several of these foregoing braces fail to directly protect the olecranon process of the ulna bone.

BRIEF SUMMARY

To overcome the aforementioned current issues, the present invention is directed to a protective sleeve for treating injury to a wearer's elbow joint comprising: a central pad, wherein the central pad further comprises an upper portion, a lower portion, a connecting portion, wherein the central pad further comprises exterior side and an interior side, wherein the central pad further comprises an upper edge, a lower edge, a left edge, and a right edge, wherein the wearer's elbow is positioned centrally under the connecting portion, wherein the connecting portion connects the upper and lower portions; a protective opening on the wearer's medial elbow region formed by the upper portion, the lower portion, and the connecting portion contoured around the wearer's medial aspect of the elbow; a cap attached on the exterior side of the central pad; a relatively thin sheet, wherein the relatively thin sheet further comprises an upper edge, a lower edge, a left edge, and a right edge, and wherein the left edge of the relatively thin sheet is affixed with the left edge of the central pad, wherein the right edge of the relatively thin sheet is affixed with the right edge of the interior side of the central pad, wherein a cylindrical space is formed between the relative thin sheet and the central pad; a cylindrical sleeve formed by the relatively thin sheet and the central pad; a first compression strip attached on the interior side within the upper portion of the central pad; a second compression strip attached on the interior side within the lower portion of the central pad; and a fastening means for securing the protective sleeve on the wearer's arm. This present invention is also directed to a method to treat injury to the medial elbow region of a wearer's elbow, the olecranon process of the elbow, and tendinitis to the medial and lateral epicondyle.

BRIEF DESCRIPTION OF THE DRAWINGS

FIG. 1 is a view of one of the embodiments of the present invention shown laid out in a flat position;

FIG. 2 is a view of one of the embodiments of the present invention shown laid out in a flat position;

FIG. 2a is a view of one of the embodiments of the present invention shown laid out in a flat position where the relative thin sheet is removed;

FIG. 3 is an elevational view of one of the embodiments of the present invention shown disposed over a wearer's right elbow while the elbow is in an extended position;

FIG. 4 is an elevational view of one of the embodiments of the present invention shown disposed over a wearer's right elbow while the elbow is in a bent position;

FIG. 5 is an elevational view of one of the embodiments of the present invention shown disposed over a wearer's right elbow while the elbow is in a bent position and illustrating the anatomy of the wearer's elbow;

FIG. 6 is a cross-sectional view taken along line 6-6 of FIG. 3;

FIG. 7 is a cross-sectional view taken along line 7-7 of FIG. 3;

FIG. 8 is a cross-sectional view taken along line 8-8 of FIG. 3;

DETAILED DESCRIPTION

Figure 9:
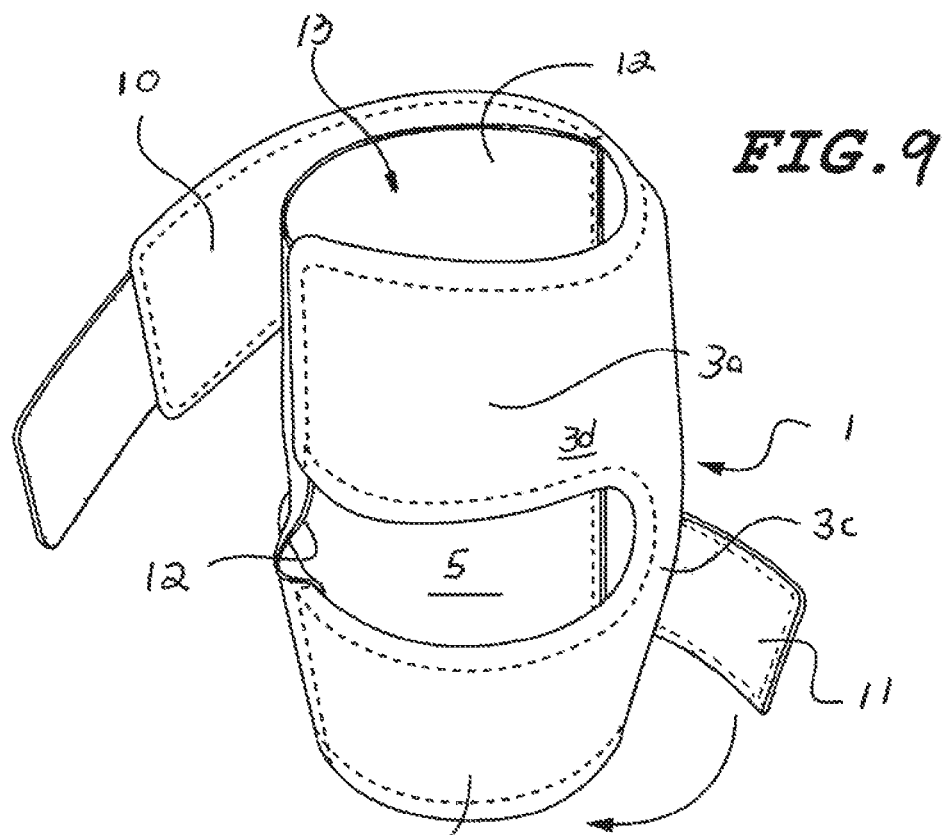
FIG. 9 is an isometric view of one of the embodiments of the present invention illustrating the medial side of the protective sleeve.

Referring now to FIGS. 1, 2, 3, 4, and 5, one of the preferred embodiments of the protective sleeve 1 is shown surrounding the right arm 2 of a wearer, with the wearer's arm 2 fully extended in FIG. 3 and the wearer's arm 2 in a bent position in FIGS. 4 and 5. Referring now to FIGS. 1 and 2, one of the preferred embodiments of the protective sleeve 1 is presented in a flattened condition to illustrate its components, with FIG. 1 showing the external side of one of the preferred embodiments of the protective sleeve 1 and FIG. 2 showing the internal side of one of the preferred embodiments of the protective sleeve 1. One of the preferred embodiments of the protective sleeve 1 comprises a central pad 3 that further comprises an upper portion 3a arranged to conform to the wearer's arm above the elbow joint 4, a lower portion 3b arranged to conform to the wearer's arm below the elbow joint 4, and a connecting portion 3c arranged to connect the upper and lower portions, 3a and 3b, respectively. The central pad 1 further comprises exterior side 3d and an interior side 3e, wherein the central pad 1 further comprises an upper edge 3f, a lower edge 3g, a right edge 3h, and a left edge 3i.

As shown in FIGS. 3, 4, and 5, when one of the preferred embodiments of the protective sleeve 1 is properly positioned over the wearer's elbow, the point of the elbow 4 (FIG. 3) is centered under the connecting portion 3c of the central pad 3.

As shown in FIGS. 1, 2, 3, 4, and 5, the upper, lower and connecting portions 3a, 3b, and 3c, respectively, form a contoured shape to define a protective opening 5 therein within which the medial elbow region of the elbow, i.e., the medial elbow region including the medial epicondyle 6, the olecranon process 7, and the space therebetween, which is prone to compression and injury due to repetitive motion or physical activity. It should be understood that the shape of the protective opening 5 is merely exemplary, and other shapes are equally suitable for protecting the medial elbow region of the wearer's elbow that is prone to injury from further compression, contact, or injury. Such compression or injury can result in inflammation and/or injury to tendons and/or soft tissue located in proximity to this space, as well as injury to the ulnar nerve 8, which passes between the medial epicondyle 6 and the olecranon process 7. For example, the protective opening 5 could be oval, or any other shape so long as the protective opening 5 surrounds and avoids contact with the medial elbow region of the elbow joint. The central pad 3 may be of any suitable thickness, such as a 0.75 inches, but other thicknesses may also suffice. The central pad 3 may be formed of any suitable cushioning material that is capable of absorbing shock energy, including Confor® foam, Poly-Fil NU-FOAM™, natural lambskin, foam, polymeric foam or polyester sponge material. The central pad 3 may be housed within a fabric, the edge of the pocket being stitch as any other conventional fabric.

Referring now to FIG. 5, a medial elbow region exists between the medial epicondyle 6 and the olecranon process 7, this medial elbow region being prone to compression and injury due to repetitive motion or physical activity. Such compression or injury can result in inflammation and/or injury to tendons and/or soft tissue located in proximity to this space, as well as injury to the ulnar nerve 8, which passes between the medial epicondyle 6 and the olecranon process 7. Mere inflammation of tendons in this space can result in injury to the ulnar nerve 8 which is also located therein. Such injuries are commonly referred to as tennis elbow, quarterback elbow, or pitcher's elbow.

Referring to FIGS. 1, 3, 4, and 5, a cap 40 is attached on the exterior side 3d on the connecting portion 3b of the central pad 3. The cap 40 is to protect further injury to the elbow 4 and from contact with hard surfaces and/or frictional forces. The cap 40 can be made of flexible material that is capable of absorbing shock energy, such as rubber or the same material of the central pad. The cap 40 can in a shape of oval, rectangle, square, or other shape as long as the cap 40 is on the elbow area to protect the elbow.

Referring to FIG. 2a, showing the internal side of one of the embodiments of the protective sleeve 1 when the relatively thin sheet 12 is removed, the central pad 3 has an interior side 3e, an upper edge 3f, a lower edge 3g, a right edge 3h, and a left edge 3i. A first compression strip 42 is attached on the interior side 3e within the upper portion 3a of the central pad 3. it is preferable to locate the first compression strip near the upper edge 3f, but the first compression strip 42 can be located lower in any area within the upper portion 3a of the central pad 3. Also, a second compression strip 44 is attached on the interior side 3e within the lower portion 3b of the central pad 3. it is preferable to locate the second compression strip near the lower edge 3g, but the second compression strip 44 can be located higher in any area within the lower portion 3b of the central pad 3. In one of the preferred embodiment of the protective sleeve, the first and second compression strips 42 and 44 can be extended to the first fastening strap 10 and the second fastening strap 11, respectively. The first and second compression strips are made of soft material, such as rubber or the same material of the central pad. The first and second compression strips have a predetermined thickness that creates an extra thicken area or hump on the interior side of the central pad 3. The purpose of the compression strips are to treat lateral and medial epicondylitis of the elbow. The compression strips work by counter-force bracing. By strapping the protective tightly around the forearm, they create a pressure on the forearm's muscles. This pressure on the forearm redirects the stressful forces away from the lateral epicondyle and tendons attached to this area. It reduces tension on the tendons at their insertion point to the lateral epicondyle by transferring force farther down the arm and into the forearm. The first and second compression strips can be attached on the interior side of the central pad fixedly or detachable, such as stitched, glued, or a loop and hook fastener.

As best shown in FIGS. 1 and 2, one of the preferred embodiments of the protective sleeve 1 comprises a first fastening strap 10 and a second fastening strap 11 as one of the means for fastening the protective sleeve 1 on the wearer's arm. The first fastening strap 10 extends from the upper portion 3*a* of the central pad 3 and can be integral with or attached to the upper portion 3*a* by any suitable means, e.g., stitching or gluing. The first fastening strap 10 is adapted to wrap around the wearer's arm above the elbow joint. Similarly, the second fastening strap 11 extends from the lower portion 3*b* of the central pad 3 and can be integral with or attached to the lower portion 3*b* by any suitable means, e.g., stitching or gluing. The second fastening strap 11 is adapted to wrap around the wearer's arm below the elbow joint. The first and second fastening straps 10, 11 preferably comprise a VELCRO® (hook or loop) surface or equivalent fastening means adapted to secure the straps 10, 11 to the outer surface of the upper and lower portions 3*a*, 3*b* of the central pad 3, respectively. FIGS. 3, 4 and 5 illustrate a lateral portion of one of the preferred embodiments of the protective sleeve 1 covering the lateral side of the wearer's arm 2, while FIG. 5 illustrates a medial portion of one of the preferred embodiments of the protective sleeve 1 covering the medial side of the wearer's arm 2. In this manner, all features of the protective sleeve are illustrated. Other ways to fasten the protective sleeve on the wearer's arm may include belt and buckle or quick-release fastener.

Referring to FIGS. 1 and 2, the first and second fastening straps 42 and 44 are extended to opposite directions. This arrangement of opposite directions of the straps generates two opposite forces, twisting and interlocking to each other's wrapping force on the wearer's arm, that works better, more convenient, and tighter than the arrangement of same directions. The first fastening straps 42 can alternatively extend from the lower portion 3*b* of the central pad 3, and reversely and alternatively, the second and second fastening straps 44 can alternatively extend from the upper portion 3*a* of the central pad 3 without hindering their fastening function.

Figure 10:
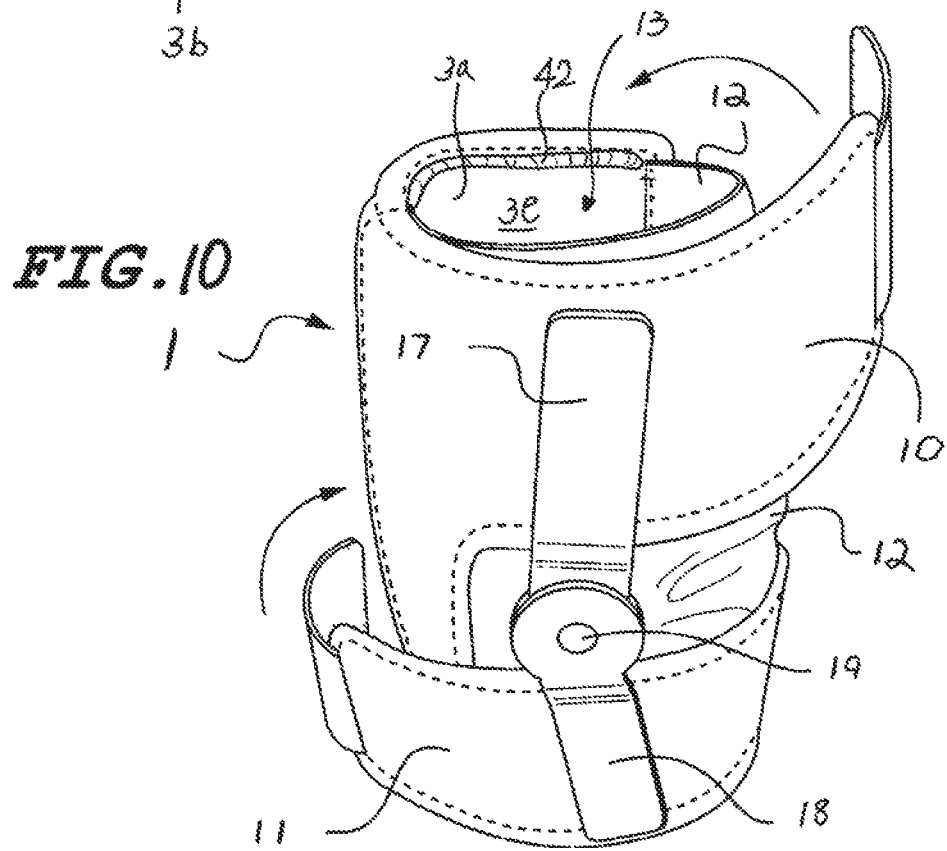
FIG. 10 is an isometric view of one of the embodiments of the present invention illustrating the lateral side of the protective sleeve.

Referring now to FIGS. 1 and 2, one of the preferred embodiments of the protective sleeve 1 comprises a relatively thin sheet 12 that may be constructed of any suitable material, e.g., from a woven fabric (similar to an ACE bandage) that is flexible, provides strength and conforms to the shape of the wearer's arm 2. Alternatively, the sheet 12 may be made of fabric-covered neoprene, or a layer of Airprene® surrounded by a layer of Coolmax™. Alternatively, the relatively thin sheet 12 may comprise inner and outer layers. The relatively thin sheet 12 may be any suitable shape. As best shown in FIG. 2, the thin sheet is generally rectangular in shape, which is exemplary only. In FIGS. 1 and 2, the relatively thin sheet 12 is shown as being affixed to the inside surface of the central pad 3. As best shown in FIG. 2, the relatively thin sheet 12 has upper edge 12*f*, lower edge 12*g*, right edge 12*h*, and left edge 12*i* along its peripheral edges to the interior side 3*e* of the central pad 3, along its peripheral edges 3*f*, 3*g*, 3*h*, and 3*i*. As best shown in FIG. 2, the left edge 12*i* of the relatively thin sheet is affixed with the left edge 3*i* of the central pad 3, and the right edge 12*h* of the relatively thin sheet 12 is affixed with the right edge 3*h* of the interior side 3*e* of the central pad 3. The left edge 12*i* of the relatively thin sheet 12 can be affixed either entirely along the left edge 3*i* or partially leaving unfixed on the left edge 3*i* around the protective opening 5. As a result, referring to FIGS. 9 and 10, the relatively thin sheet 12 and the central pad 3 form a cylindrical sleeve 13 that has a cylindrical space 14 through which the wearer can insert his arm 2. This cylindrical sleeve 13 formed by the relatively thin sheet 12 and central pad 3 is also illustrated in the cross-sections of FIGS. 6 through 8. The relatively thin sheet 12 may comprises a hypoallergenic material such as silk, wool, cotton, or a combination thereof.

As best shown in FIGS. 1, 2, 3, 4, and 5, one of the preferred embodiments of the protective sleeve 1 comprises at least one light pre-shaped lateral support assembly 16 located along the lateral side of one of the preferred embodiments of the protective sleeve 1 to provide enhanced support to one of the preferred embodiments of the protective sleeve 1. Also referring to FIGS. 11, 12, and 13, the at least one lateral support assembly 16 further comprises an upper segment 17, a lower segment 18, a linkage 19 coupled with the upper segment 17 and the lower segment 18, a means for attaching the at least one lateral support assembly 16 to the first fastening strap 10 and to the second fastening strap 11, wherein the upper segment 17 and the lower segment 18 are rotatable relatively around the linkage 19. The lateral support assembly 16 preferably is positioned along the lateral side of the wearer's arm to add stability and aid in mobility of one of the preferred embodiments of the protective sleeve 1. The lateral support assembly 16 can be sewn in place or be removable and fastened into place with flexible hook and loop components of a VELCRO® fastening system or other equivalent fastening systems, such as buttons, sewn-in pockets or any other means to secure the lateral support assembly 16. One or both ends of the lateral support assembly 16 can be fastened into place by the aforementioned method. This lateral support assembly 16 could be utilized to limit the mobility of the elbow joint, stabilize the elbow joint's range of motion and/or prevent the elbow joint from hyperextension. A second lateral support assembly (not shown), that can be sewn into place or be removable and fastened into place using similar securement devices could also be placed along the medial aspect of one of the preferred embodiments of the protective sleeve 1 over the protective opening 5 to limit the mobility of the elbow joint, stabilize the elbow joint's range of motion and/or prevent the elbow joint from hyperextension.

Figure 11:
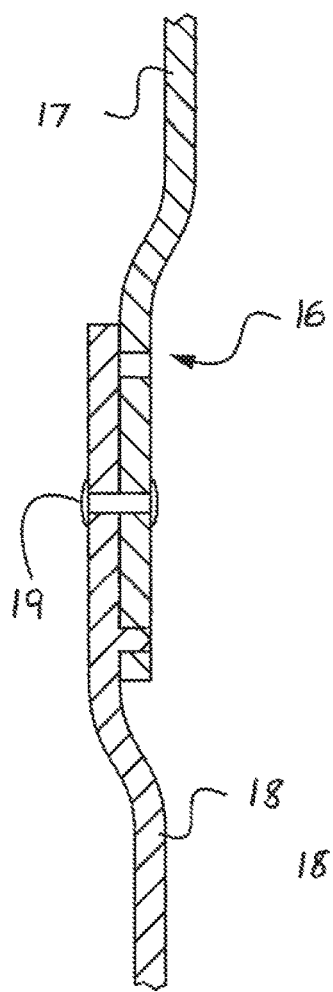
FIG. 11 is a cross-sectional view taken along line 11-11 of FIG. 3.
Figure 12:
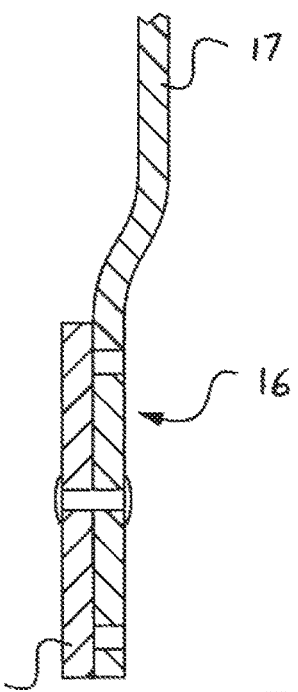
FIG. 12 is a cross-sectional view taken along line 12-12 of FIG. 4.
Figure 13:
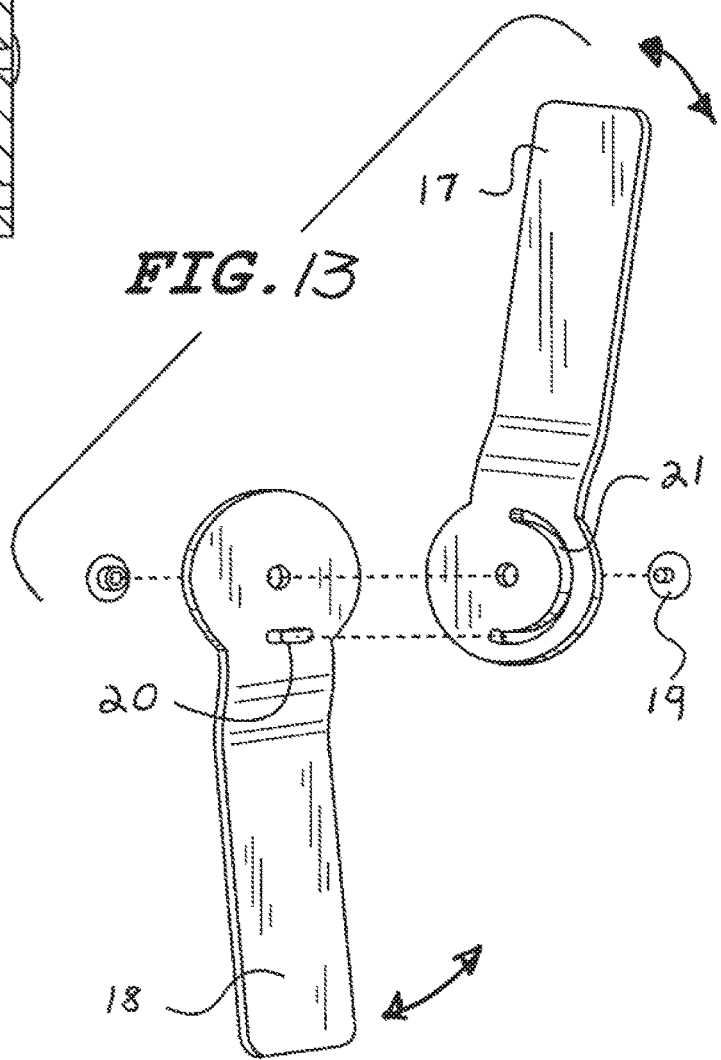
FIG. 13 is a view of the component parts of a lateral support assembly of one of the embodiments of the present invention.

The component parts of the lateral support assembly 16 in one of the embodiments of the protective sleeve are best shown in FIGS. 11, 12, and 13, wherein an upper segment 17 is joined to a lower segment 18 by using any suitable fastening mechanism, e.g., a rivet 19. It should be understood that the upper segment 17 and lower segment 18 of the lateral support assembly 16 may be held together by other suitable fastening mechanisms, e.g., nut and bolt. The lower segment 18 comprises a finger 20 which is arranged to travel within a curved through slot 21 located on the upper segment 17 during bending of one of the preferred embodiments of the protective sleeve 1. Although the figures presented show the third embodiment protective sleeve 1 positioned over a wearer's right arm, it should be understood that the protective sleeve can be turned over to insert the wearer's left arm through the opposite end of the cylindrical sleeve.

As best shown by one of the embodiments of the protective sleeve in FIGS. 3, 4, and 5, with the arm 2 of the wearer inserted through the cylindrical sleeve 13 formed by the relatively thin sheet 12 and the central pad 3, one of the preferred embodiments of the protective sleeve 1 is positioned for use over the elbow with the relatively thin sheet 12 positioned over the crease of the elbow and the connecting portion 3*c* positioned over the point of the elbow 4. In this orientation, one of the preferred embodiments of the protective sleeve 1 will bend most easily during the wearer bending his arm 2. With the protective sleeve in this orientation, the protective opening 5 will be positioned over the area of the elbow that is prone to such injury as discussed above, i.e., the medial epicondyle 6 and its surrounding soft tissue structures, along with the ulnar nerve 8 as the ulnar nerve passes between the medial epicondyle 6, and the olecranon process 7. The protective opening 5 is situated over these areas such that the medial epicondyle 6 is situated towards the distal end of the protective opening 5. In this manner, no matter how the wearer positions his or her arm, especially during sleeping, the injured area of the elbow within the protective opening 5 remains isolated from contact and friction. As the arm is flexed, extended, pronated, or supinated, there is no contact by one of the preferred embodiments of the protective sleeve 1 with the area within the protective opening 5 that will cause friction or rubbing on the injured portion of the elbow.

Referring to FIGS. 3, 4, and 5, as one of the embodiments of the protective sleeve shows, when applying one of the preferred embodiments of the protective sleeve 1, the wearer simply extends his hand and arm through the cylindrical sleeve formed by the relatively thin sheet 12 and the central pad 3 so that one of the preferred embodiments of the protective sleeve 1 is positioned radially about the wearer's arm 2 with the point of the elbow 4 centered under the connecting portion 3c and the relatively thin sheet 12 situated on the crease of the elbow (opposite the point of the elbow).

It is an object of the present invention to provide a protective sleeve that overcomes the shortcomings of the above-mentioned braces. It is a further object of the present invention to provide a protective sleeve that adequately treats and prevents injuries to the cubital tunnel and surrounding soft tissues, ulnar nerve compression and/or injury in the cubital tunnel, tennis elbow (specifically pertaining to tendonitis of the medial or lateral epicondyle of the humerus), and or other similar muscular and nerve disorders in the region of the elbow. The present invention would achieve this by distributing pressure, strain and friction away from injured area of the elbow by providing padding to the surrounding structures. Thereby, through selective isolation of the targeted portion of the elbow joint, the protective sleeve of the present invention will promote healing and prevent future injuries.

It is still a further object the present invention to provide a protective sleeve that is flexible, easy to handle, and can be self-applied by individuals suffering from the aforementioned problems. It is an additional object of the present invention to provide a protective sleeve that is adaptable to various movements, is arranged to be useful in different positions, can be worn on either arm and is elastic, and flexible. It is still an additional object of this invention to provide cushioning to the olecranon process of the ulna bone and prevent and treat injuries to this area.

It is understood that the protective sleeve and its constituent parts described herein is an exemplary indication of a preferred embodiment of the invention, and is given by way of illustration only. In other words, the concept of the present invention may be readily applied to a variety of preferred embodiments, including those disclosed herein. While the invention has been described in detail and with reference to specific examples thereof, it will be apparent to one skilled in the art that various changes and modifications can be made therein without departing from the spirit and scope thereof.

What is claimed:

1. A protective sleeve for treating injury to a wearer's elbow and elbow joint of wearer's arm, comprising:
   a. a central pad, wherein the central pad further comprises an upper portion, a lower portion, a connecting portion, wherein the central pad further comprises an exterior side and an interior side, wherein the central pad further comprises an upper edge, a lower edge, a left edge, and a right edge, wherein the connecting portion is configured to be centrally on the wearer's elbow, wherein the connecting portion connects the upper and lower portions;
   b. a protective opening for wearer's medial elbow region formed by the upper portion, the lower portion, and the connecting portion contoured around the wearer's medial elbow region;
   c. a cap attached on the exterior side of the central pad;
   d. a relatively thin sheet, wherein the relatively thin sheet further comprises an upper edge, a lower edge, a left edge, and a right edge, wherein the left edge of the relatively thin sheet is affixed with the left edge of the central pad, wherein the right edge of the relatively thin sheet is affixed with the right edge of the interior side of the central pad, and wherein a cylindrical space is formed between the relative thin sheet and the central pad;
   e. a cylindrical sleeve formed by the relatively thin sheet and the central pad;
   f. a first compression strip attached on the interior side within the upper portion of the central pad, wherein the first compression strip creates a first hump;
   g. a second compression strip attached on the interior side within the lower portion of the central pad, wherein the second compression strip creates a second hump; and
   h. a fastening means for securing the protective sleeve on the wearer's arm.

2. The protective sleeve of claim 1, wherein the relatively thin sheet further comprises a flexible woven fabric material.

3. The protective sleeve of claim 1, wherein the relatively thin sheet further comprises a hypoallergenic materials.

4. The protective sleeve of claim 1, wherein the central pad comprises a polymeric foam or polyester sponge material.

5. The protective sleeve of claim 1, wherein the central pad comprises a material capable of absorbing shock energy.

6. The protective sleeve of claim 1, wherein the cap comprises a material capable of absorbing shock energy.

7. The protective sleeve of claim 1, wherein the fastening means further comprises a first fastening strap having a first end attached to the upper portion or alternatively attached to the lower portion of the central pad and a second end opposite to the first end extending out of the upper portion or alternatively out of the lower portion of the central pad; a second fastening strap having a first end attached to the lower portion or alternatively to the upper portion of the central pad and a second end opposite to the first end extending out of the lower portion or alternatively of the upper portion of the central pad; and wherein the first fastening strap extends oppositely to the second fastening strap.

8. The protective sleeve of claim 7, wherein the first compression strip extends to the first fastening strap, and wherein the second compression strip extends to the second fastening strap.

9. The protective sleeve of claim 7, further comprises at least one loop and hook fastener attached on the second end of the first fastening strap and at least another one loop and hook fastener attached on the second end of the second fastening strap.

10. The protective sleeve of claim 7, further comprising at least one lateral support assembly, wherein the at least one lateral support assembly further comprises an upper segment, a lower segment, a linkage coupled with the upper segment and the lower segment, a means for attaching the at least one lateral support assembly to the first fastening strap and to the second fastening strap, wherein the upper segment and the lower segment are rotatable relatively around the linkage.

11. The protective sleeve of claim 10, wherein the at least one lateral support assembly is detachable from the first fastening strap and the second fastening strap.

12. A protective sleeve for treating injury to a wearer's elbow and elbow joint of wearer's arm, comprising:
   a. a central pad, wherein the central pad further comprises an upper portion, a lower portion, a connecting portion, wherein the central pad further comprises an exterior side and an interior side, wherein the central pad further comprises an upper edge, a lower edge, a left edge, and a right edge, wherein the connecting portion is configured to be centrally on the wearer's elbow, wherein the connecting portion connects the upper and lower portions;
   b. a protective opening one wearer's medial elbow region formed by the upper portion, the lower portion, and the connecting portion contoured around the wearer's medial elbow region;
   c. a cap attached on the exterior side of the central pad;
   d. a relatively thin sheet, wherein the relatively thin sheet further comprises an upper edge, a lower edge, a left edge, and a right edge, wherein the left edge of the relatively thin sheet is affixed with the left edge of the central pad, wherein the right edge of the relatively thin sheet is affixed with the right edge of the interior side of the central pad, and wherein a cylindrical space is formed between the relative thin sheet and the central pad;
   e. a cylindrical sleeve formed by the relatively thin sheet and the central pad;
   f. a first compression strip attached on the interior side within the upper portion of the central pad, wherein the first compression strip creates a first hump;
   g. a second compression strip attached on the interior side within the lower portion of the central pad, wherein the second compression strip creates a second hump;
   h. a first fastening strap having a first end attached to the upper portion or alternatively attached to the lower portion of the central pad and a second end opposite to the first end extending out of the upper portion or alternatively out of the lower portion of the central pad;
   i. a second fastening strap having a first end attached to the lower portion or alternatively to the upper portion of the central pad and a second end opposite to the first end extending out of the lower portion or alternatively of the upper portion of the central pad; and wherein the first fastening strap extends oppositely to the second fastening strap.

13. The protective sleeve of claim 12, further comprising at least one lateral support assembly, wherein the at least one lateral support assembly further comprises an upper segment, a lower segment, a linkage coupled with the upper segment and the lower segment, a means for attaching the at least one lateral support assembly to the first fastening strap and to the second fastening strap, wherein the upper segment and the lower segment are rotatable relatively around the linkage.

14. A method of using a protective sleeve to treat injury to a wearer's elbow and elbow joint of wearer's arm, comprising the steps of:
   a. providing a protective sleeve, comprising a central pad, wherein the central pad further comprises an upper portion, a lower portion, a connecting portion, wherein the central pad further comprises an exterior side and an interior side, wherein the central pad further comprises an upper edge, a lower edge, a left edge, and a right edge, wherein the connecting portion is configured to be centrally on the wearer's elbow, wherein the connecting portion connects the upper and lower portions; a protective opening one wearer's medial elbow region formed by the upper portion, the lower portion, and the connecting portion contoured around the wearer's medial elbow region; a cap attached on the exterior side of the central pad; a relatively thin sheet, wherein the relatively thin sheet further comprises an upper edge, a lower edge, a left edge, and a right edge, wherein the left edge of the relatively thin sheet is affixed with the left edge of the central pad, wherein the right edge of the relatively thin sheet is affixed with the right edge of the interior side of the central pad, and wherein a cylindrical space is formed between the relative thin sheet and the central pad; a cylindrical sleeve formed by the relatively thin sheet and the central pad; a first compression strip attached on the interior side within the upper portion of the central pad; a second compression strip attached on the interior side within the lower portion of the central pad; and a fastening means for securing the protective sleeve on the wearer's arm; wherein the first compression strip creates a first hump; and wherein the second compression strip creates a second hump;
   b. allowing the wearer's arm through the cylindrical sleeve;
   c. positioning the wearer's medial elbow region under the protective opening to protect the medial aspect from contact, pressure and friction; and
   d. fastening the protective sleeve on the wearer's arm.

15. The method of claim 14, wherein the fastening means further comprises a first fastening strap having a first end attached to the upper portion or alternatively attached to the lower portion of the central pad and a second end opposite to the first end extending out of the upper portion or alternatively out of the lower portion of the central pad; a second fastening strap having a first end attached to the lower portion or alternatively to the upper portion of the central pad and a second end opposite to the first end extending out of the lower portion or alternatively of the upper portion of the central pad; and wherein the first fastening strap extends oppositely to the second fastening strap.

16. The method of claim 15, further comprising at least one lateral support assembly, wherein the at least one lateral support assembly further comprises an upper segment, a lower segment, a linkage coupled with the upper segment and the lower segment, a means for attaching the at least one lateral support assembly to the first fastening strap and to the second fastening strap, wherein the upper segment and the lower segment are rotatable relatively around the linkage.

* * * * *